United States Patent [19]

Mikkelsen

[11] Plant 4,192

[45] Jan. 17, 1978

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 764,012

[22] Filed: Jan. 31, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A novel Impatiens plant having white blossoms and sharply variegated foliage.

1 Drawing Figure

1

The present invention relates to a new and distinctive cultivar of Impatiens plant, botanically known as Impatiens and known by the cultivar name Monticello. The new cultivar was developed by me through controlled breeding by crossing my unpatented seedling numbered 74-143-1 (seed parent) with the unpatented cultivar Arabesque (pollen parent), a cultivar of the U.S. Department of Agriculture. Asexual reproduction of terminal or stem cuttings by me at Ashtabula, Ohio has shown that the unique features of this new Impatiens are stabilized and are reproduced true to type in successive propagations.

The following characteristics distinguish the new cultivar from both its parent varieties and other cultivated Impatiens of this type known and used in the floriculture industry:

1. Although the general appearance is somewhat similar to Patriot, the foliage is generally smaller and less coarse in appearance than that of Patriot, and the same comments apply with respect to the pollen parent Arabesque. Patriot is disclosed in my pending application Ser. No. 764,011 filed Jan. 31, 1977.
2. The variegation pattern is sharper, more distinct than that of Patriot, or the pollen parent Arabesque.
3. The foliage color is lighter than Patriot.
4. The overall growth is more free, has better branching and is faster than Patriot; cutting production is superior to Patriot or Arabesque.
5. Flowers are of comparable size to Patriot; however, the top petal is more isolated than the top petal of Patriot, and the apice of the top petal is pointed in Monticello but tends to be notched in Patriot.
6. Monticello is more tolerable to outdoor environments than is Patriot or Arabesque.
7. Monticello has been demonstrated to be useful as a pot plant if given maximum light exposure in a south window.

The accompanying colored photograph illustrates the overall appearance of the new cultivar and shows the colors as true as it is reasonably possible to obtain in a colored reproduction of this type. The plant illustrated was grown in a 5" clay pot and given a tip pinch in August, 1975, with the photograph being taken in October, 1975.

The following is a detailed description of my new Impatiens cultivar based on plants produced under commercial practices in greenhouses at Mikkelsens Inc., Ashtabula, Ohio. Color references are made to the Royal Horticultural Society Colour Chart except

2 where general terms of ordinary dictionary significance are used.

Parentage: A controlled pollination of Mikkelsen seedling 74-143-1 as the seed parent crossed with the cultivar Arabesque (U.S.D.A.) as the pollen parent.

Propagation:

*Type cutting.*—Tip cuttings 2–3 cm. long.

*Time to visible rooting.*—10–12 days at 21° C summer, 12–15 days at 20° C winter.

*Rooting habit.*—Rapid, profuse primary and secondary roots, dendritic pattern.

Plant description:

*Form.*—Generally upright, semi-compact, tending toward open.

*Habit of growth.*—Medium to fast, vigorous, nearly upright.

*Foliage description.*—Medium green, medium size, clearly variegated, durable, flat with slight tendency to revolute. Size: 4 cm. to 5 cm. wide by 10 cm. to 12 cm. long with petiole up to 3 cm. long. Shape: Generally elliptical usually symmetrical but with one side being unbalanced occasionally; apex acute, base acute. Texture: Crisp, glabrous, rugose. Margin: Entire, rather obscure ciliolate. Color: Young foliage: nearly same coloration as the mature foliage. Mature foliage, top side: outer margins yellow green 147B, inner area yellow orange 2DC-D; under side: outer margins yellow green 148B to 147C, inner area yellow orange 20D to 19D. Venation: Pinnately, arcuate.

Flowering description:

*Flowering habits.*—Progressively around the whorl of leaves, generally one flower per leaf, 6–7 leaves per whorl.

*Natural flowering season.*—Flowering is indeterminate, occurring in all seasons.

*Flower buds.*—Typical for New Guinea Impatiens, symmetrically conical, covered by 2 true sepals and one scale like sepal on the back side of the top petal, and an emerging hollow greenish white to translucent spur.

*Flowers borne.*—Single on a white pedicel up to 5 cm. long and 2 mm. in diameter at the base.

*Quantity of flowers.*—Near normal for New Guinea Impatiens but not appearing floriferous as white flowers usually do not have good keeping qualities.

*Petals.*—Shape: Nearly heart shaped, blunt at base. Color: Top side in winter when opening white, under side white. Number of petals: 5, top largest, other four nearly equal. Size of petals: up to 3 cm. across, flowers up to 6 cm. in diameter.

*Reproductive organs.*—Stamens: One in number. Anther shape: Hooded over pistil, white in color. Pollen color: White. Pistils: Stigma shape: flat, circular, irregular surface, translucent green in color. Style color: Light green. Ovaries: One in number, size 4 mm., color green.

I claim:

1. A new and distinct cultivar of Impatiens known by the cultivar name Monticello and particularly characterized as to uniqueness by the combined characteristic of distinct variegated pattern of foliage; excellent and fast growth; good branching habit and white flowers in which the top petal tends to be spaced or isolated from the remaining four petals, and its tolerance to outdoor environments.

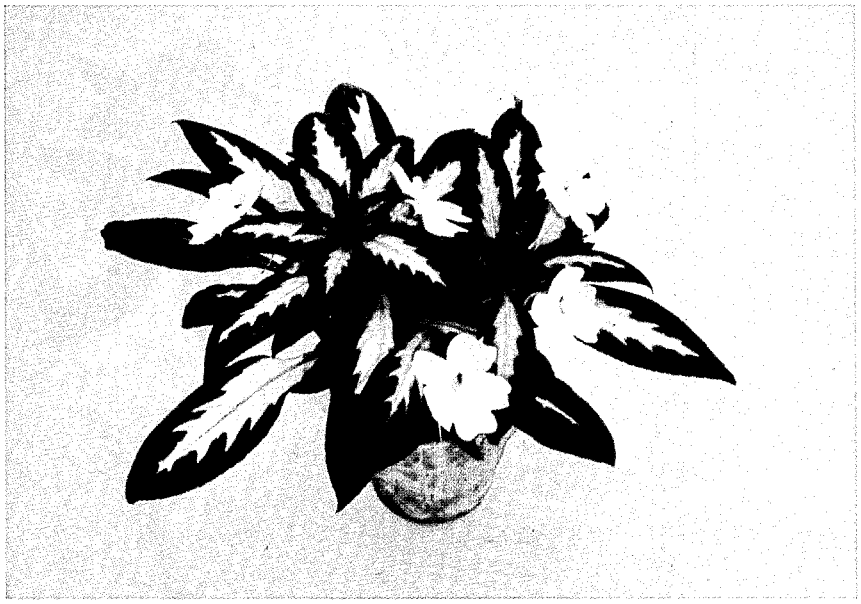

* * * * *